United States Patent
Chen et al.

(10) Patent No.: US 11,609,807 B2
(45) Date of Patent: Mar. 21, 2023

(54) COMPUTING TASK MANAGEMENT AND ANALYSIS SYSTEM FOR MOLECULAR FORCE FIELD PARAMETER BUILDING AND OPERATION METHOD THEREOF

(71) Applicant: SHENZHEN JINGTAI TECHNOLOGY CO., LTD., Guangdong (CN)

(72) Inventors: Yongpan Chen, Guangdong (CN); Yang Liu, Guangdong (CN); Wanchao Zhang, Guangdong (CN); Cuihua Song, Guangdong (CN); Fei Han, Guangdong (CN); Shuhao Wen, Guangdong (CN); Jian Ma, Guangdong (CN); Lipeng Lai, Guangdong (CN)

(73) Assignee: SHENZHEN JINGTAI TECHNOLOGY CO., LTD., Guangdong (CN)

( * ) Notice: Subject to any disclaimer, the term of this patent is extended or adjusted under 35 U.S.C. 154(b) by 443 days.

(21) Appl. No.: 16/630,467

(22) PCT Filed: Dec. 21, 2018

(86) PCT No.: PCT/CN2018/122777
§ 371 (c)(1),
(2) Date: Jan. 13, 2020

(87) PCT Pub. No.: WO2020/029513
PCT Pub. Date: Feb. 13, 2020

(65) Prior Publication Data
US 2021/0064427 A1    Mar. 4, 2021

(51) Int. Cl.
*G06F 9/54* (2006.01)
*H04L 67/10* (2022.01)
(Continued)

(52) U.S. Cl.
CPC ............. *G06F 9/547* (2013.01); *G06F 9/54* (2013.01); *G16B 5/00* (2019.02); *G16B 15/00* (2019.02);
(Continued)

(58) Field of Classification Search
None
See application file for complete search history.

(56) References Cited

FOREIGN PATENT DOCUMENTS

| CN | 101131707 | 2/2008 |
|---|---|---|
| CN | 107239675 | 10/2017 |

(Continued)

OTHER PUBLICATIONS

Vanquelef et al., "R.E.D. Server: a web service for deriving RESP and ESP charges and building force field libraries for new molecules and molecular fragments", May 23, 2011, Nucleic Acids Research, vol. 39, pp. W511-W517. (Year: 2011).*

(Continued)

*Primary Examiner* — Qing Yuan Wu
(74) *Attorney, Agent, or Firm* — Muncy, Geissler, Olds & Lowe, P.C.

(57) ABSTRACT

The invention belongs to the technical field of the molecular force field and particularly relates to a computing task management and analysis system for molecular force field parameter building and an operation method thereof. The system comprises a computing result analysis module and a computing task management module, the computing result analysis module is connected with the computing task management module, and the computing task management module is connected with a force field building computing server through a cloud computing interface. The operation method comprises: (1) selecting a molecular force field building computing templates; (2) selecting a computing task submitting platform and submitting computing tasks;

(Continued)

(3) retrieving computing results; and (4) analyzing the computing results. According to the invention, since force field building system users mainly including researchers do not have powerful open interface development capacity commonly, a convenient cloud computing calling interface is provided, and the force field building speed is improved; the system provides full-view and visual effects; an interactive analysis mode is provided for the force field building computing results, which facilitates quick location of a computing exception; and automatic task processing and analysis are supported.

2 Claims, 6 Drawing Sheets

(51) Int. Cl.
    *G16C 10/00*     (2019.01)
    *G16B 5/00*     (2019.01)
    *G16B 15/00*     (2019.01)
    *G06N 20/00*     (2019.01)

(52) U.S. Cl.
    CPC .............. *G16C 10/00* (2019.02); *H04L 67/10* (2013.01); *G06N 20/00* (2019.01)

(56) References Cited

FOREIGN PATENT DOCUMENTS

| CN | 107368700 | 11/2017 |
|---|---|---|
| CN | 108664729 | 10/2018 |
| CN | 108804863 | 11/2018 |
| CN | 108846253 | 11/2018 |
| CN | 109637592 | 4/2019 |

OTHER PUBLICATIONS

Pronk et al., "GROMACS 4.5: a high-throughput and highly parallel open source molecular simulation toolkit", Feb. 13, 2013, Oxford University Press, vol. 29 No. 7, pp. 845-854. (Year: 2013).*
Lawrenz et al., "Cloud computing approaches for prediction of ligand binding poses and pathways", Jan. 22, 2015, Scientific Reports, pp. 1-5. (Year: 2015).*
Iqbal et al., "Augmenting High-Performance Mobile Cloud Computations for Big Data in AMBER", Apr. 2, 2018, Wiley, vol. 2018, pp. 1-12. (Year: 2018).*
Dupradueau et al., "The R.E.D. tools: advance in RESP and ESP charge derivation and force field library building", Apr. 2010, Physical Chemistry Chemical Physics, pp. 7821-7839. (Year: 2010).*
"International Search Report (Form PCT/ISA/210) of PCT/CN2018/122777," dated Sep. 30, 2019, pp. 1-5.

* cited by examiner

COMPUTING TASK MANAGEMENT AND ANALYSIS SYSTEM FOR MOLECULAR FORCE FIELD PARAMETER BUILDING AND OPERATION METHOD THEREOF

CROSS-REFERENCE TO RELATED APPLICATION

This application is a 371 application of International PCT application serial no. PCT/CN2018/122777, filed on Dec. 21, 2018. The entirety of the above-mentioned patent application is hereby incorporated by reference herein and made a part of this specification.

BACKGROUND OF THE INVENTION

Technical Field

The present invention belongs to the technical field of the molecular force field and particularly relates to a computing task management and analysis system for molecular force field parameter building and an operation method thereof.

Description of Related Art

In the traditional molecular force field building method, a computer program (i.e., a parameterized system) is usually used to implement the submission and management of automatic computing tasks, and analysis of computing results to complete the automatic building of a molecular force field. Generally, main modules of such systems are for: automatic submission of computing tasks, management of computing tasks, static analysis of computing results, and data management of force field parameters. In general, the traditional molecular force field building system provides automatic submission, management, and static analysis functions for building computing tasks, which meets the basic needs of molecular force field building workers.

With the development of pharmaceuticals, materials and chemistry industries, more and more types of molecules are involved. Traditional molecular force fields are increasingly unable to meet the needs of research and development in terms of accuracy and coverage. In addition, computing methods based on the traditional force field building method and computing methods based on the local or a server cluster have been unable to meet the needs of a general force field building that can cover a larger chemical space.

The building process of force field parameters is usually not linear, and the data structure often presents a data structure in the form of a graph. The traditional computing task management and presentation methods are based on the list management of a certain attribute of a task and cannot visually correspond to the parameterized graph data structure of an actual force field, causing low management efficiency. In addition, a large amount of data analysis is often designed for the computing tasks in the building of the force field parameters. Usually, one task will be designed with thousands of conformations. Traditional static analysis methods cannot well support the analysis of high-volume conformations, and also limit the expansion of automatic building.

BRIEF SUMMARY OF THE INVENTION

Aiming at the above technical problems, the present invention provides a computing task management and analysis system for molecular force field parameter building and an operating method thereof, which can meet the computing management and analysis requirements of molecular force field building under the new technical background.

Specific Technical Solutions are as Follows:

A computing task management and analysis system for molecular force field parameter building, comprising a computing result analysis module and a computing task management module, wherein the computing result analysis module is connected with the computing task management module, and the computing task management module is connected with a force field building computing server through a cloud computing interface.

The computing result analysis module involves interactive analysis, custom analysis, and automatic analysis. The computing task management module involves computing task submission, graph data structure view, computing task template setting, computing task result retrieving, and computing path setting; the task result retrieving is connected to the computing result analysis module, and the computing task submission is connected to the cloud computing interface.

An operation method of the computing task management and analysis system, comprising the following steps:

(1) Selecting Molecular Force Field Building Computing Templates

For different types of molecules, different parameters will need to be adjusted in the case of submission of a molecular force field building computing task. The system automatically recommends computing parameters based on an input molecular type through a machine learning algorithm. Furthermore, the user may also adjust the parameters as needed; if automatic computing task submission is performed, a molecular computing path may also be set.

(2) Selecting a Computing Task Submitting Platform and Submitting the Computing Task The system submits the computing task to a local computing server or cluster, supercomputing centers, and cloud services;

(3) Retrieving Computing Results

After the computing task is completed, the system supports retrieving the computing result data to the local, clearing computing data at the server or cloud, and backing up important process data to the local.

After the computing task is retrieved, it will be displayed according to the graph data structure of the force field parameters and with the force field parameters as indexes.

(4) Analyzing the Computing Results

After the computing results are retrieved, the system can analyze the computing results.

If an interactive analysis function is applied, data exceptions of the results can be quickly located and analyzed by using an analysis template.

If a custom analysis function is applied, charts can be generated for analysis by analyzing the types of graphs and data displayed in a custom manner.

If an automatic analysis function is applied, it can cooperate with the automatic computing task submission to determine whether the tasks meet the standards.

In the computing task management and analysis system for molecular force field parameter building and the operation method thereof, provided by the present invention, the core of computing task management is the management and scheduling of computing tasks based on the characteristics of the actual data structure built by the molecular force field. On the other hand, the computing results are interactively analyzed, which is convenient for users to quickly locate the problem and quickly obtain the information of each data exception; moreover, the automatic building process is supported through function calling.

In the computing task management and analysis system for molecular force field parameter building and the operation method thereof, provided by the present invention, since force field building system users mainly including researchers do not have powerful open interface development capacity commonly, the system provide a convenient cloud computing calling interface, which facilitates the calling of a greater computing power and improves the force field building speed; since computing tasks are managed in the form of graph data structures with force field building characteristics, the system provides full-view and visual effects; an interactive analysis mode is provided for the force field building computing results, which facilitates quick location of a computing exception; and automatic task processing and analysis are supported.

DETAILED DESCRIPTION OF THE INVENTION

The specific technical solution of the present invention will be described with reference to the embodiments.

Figure 1:
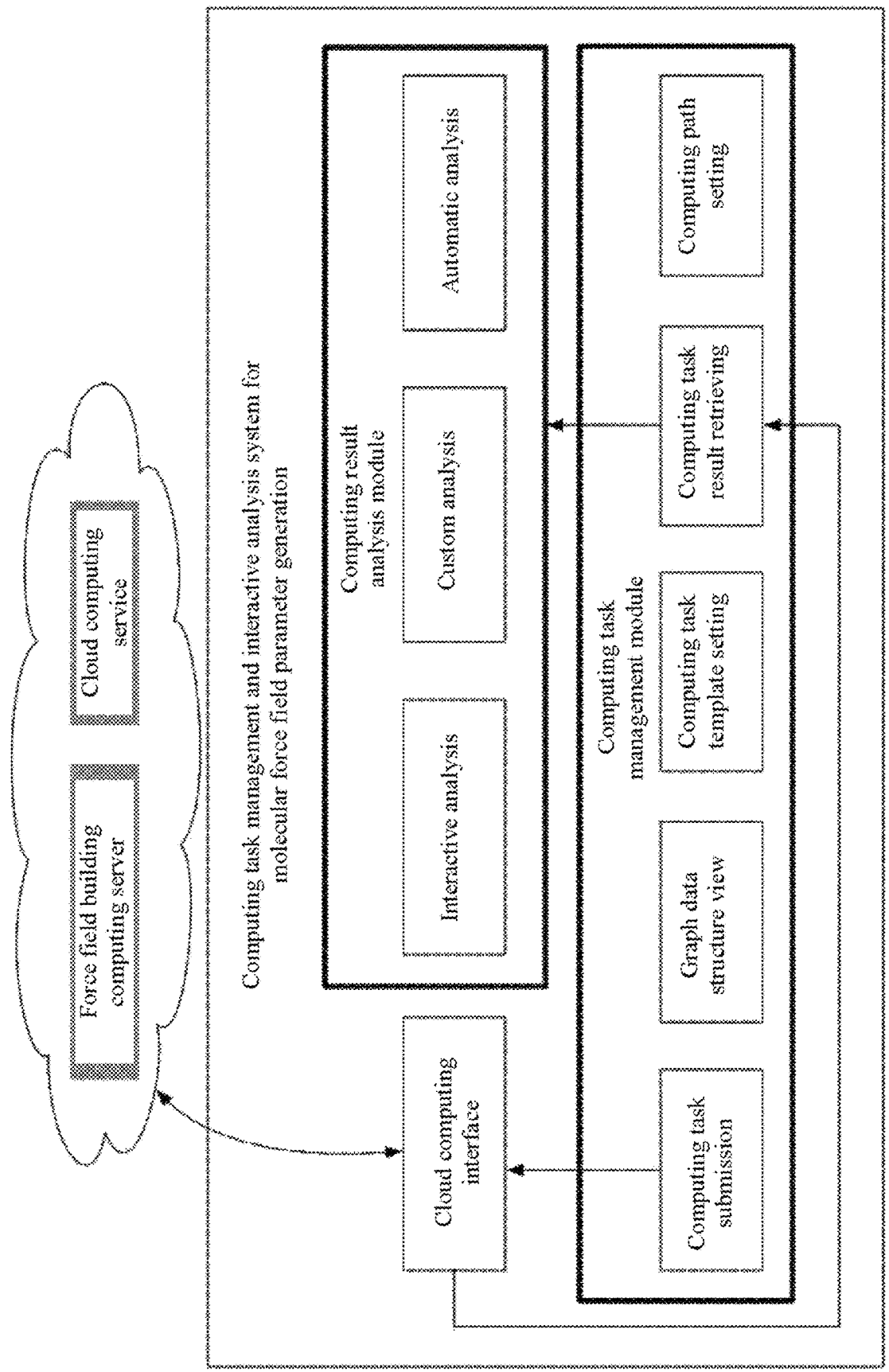
FIG. 1 is a schematic structural diagram of a system of a structure according to the present invention.

As shown in FIG. 1, a computing task management and analysis system for molecular force field parameter building comprises a computing result analysis module and a computing task management module, wherein the computing result analysis module is connected with the computing task management module, and the computing task management module is connected with a force field building computing server through a cloud computing interface. The computing result analysis module involves interactive analysis, custom analysis, and automatic analysis. The computing task management module involves computing task submission, graph data structure view, computing task template setting, computing task result retrieve, and computing path setting; the task result retrieving is connected to the computing result analysis module, and the computing task submission is connected to the cloud computing interface.

Figure 2:
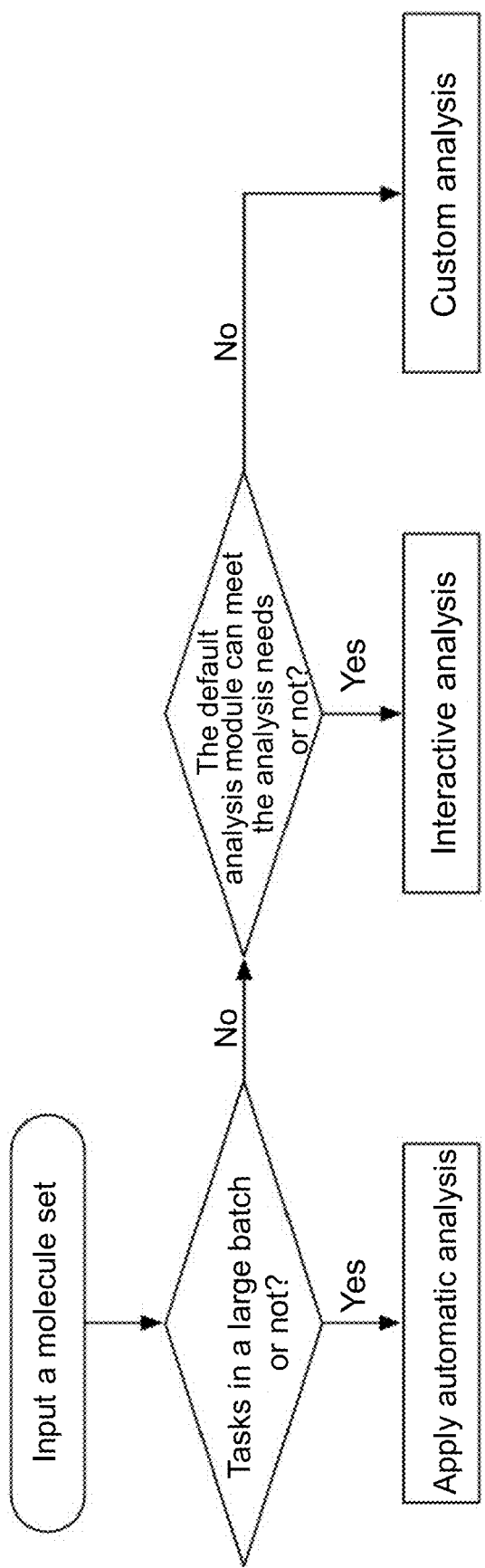
FIG. 2 is a flowchart under different analysis scenario conditions according to the present invention.

According to different application scenarios, this system can apply two modes of manual analysis and automatic analysis. The manual analysis here is divided into interactive analysis and custom analysis. Usually, automatic analysis is applied when high-volume computing is required; interactive analysis is applied when the system's own analysis template can meet the analysis needs; custom analysis is applied when personalized analysis is needed, as shown in FIG. 2.

Figure 3:
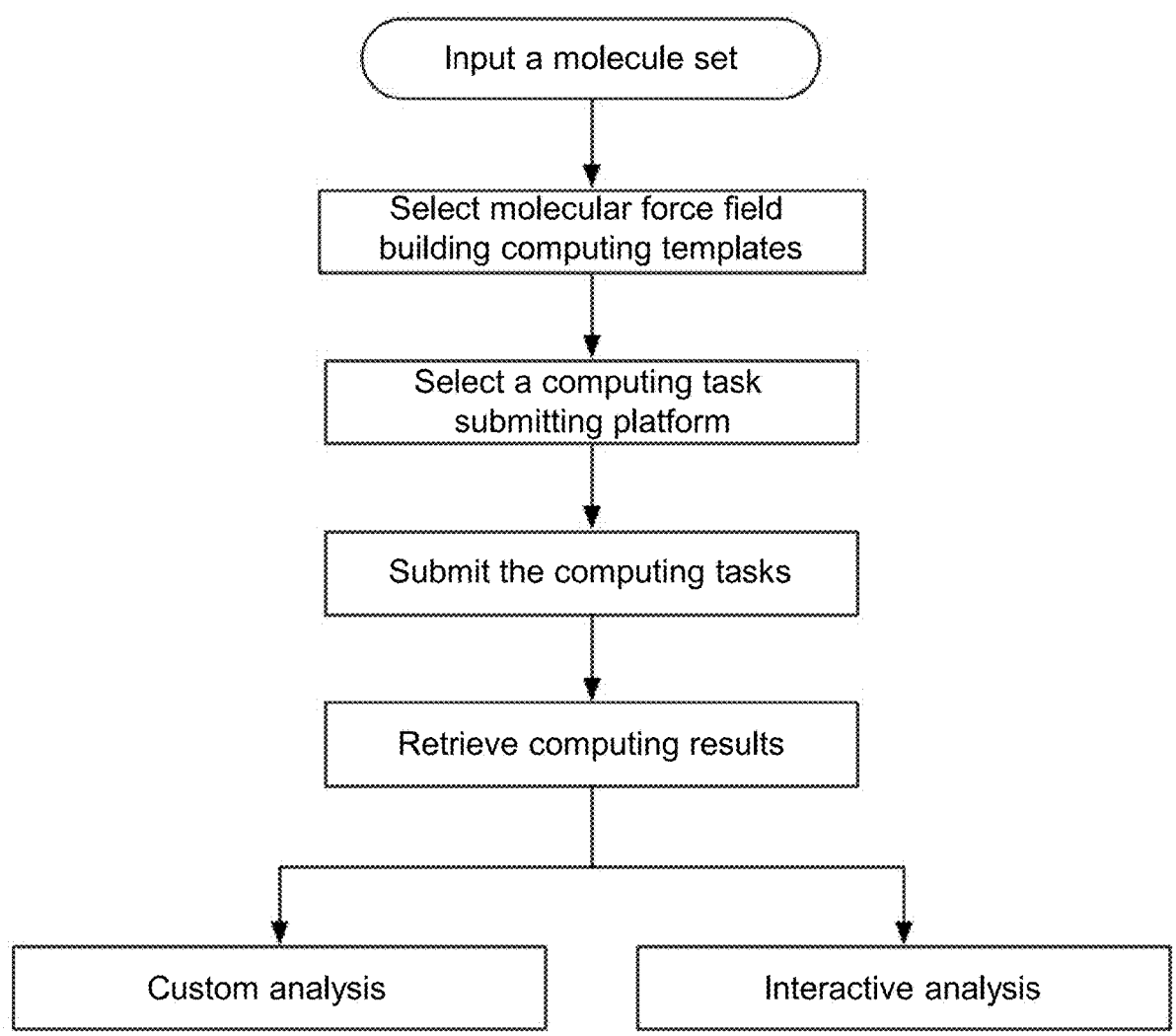
FIG. 3 is a flowchart under a manual analysis scenario according to the present invention.
Figure 4:
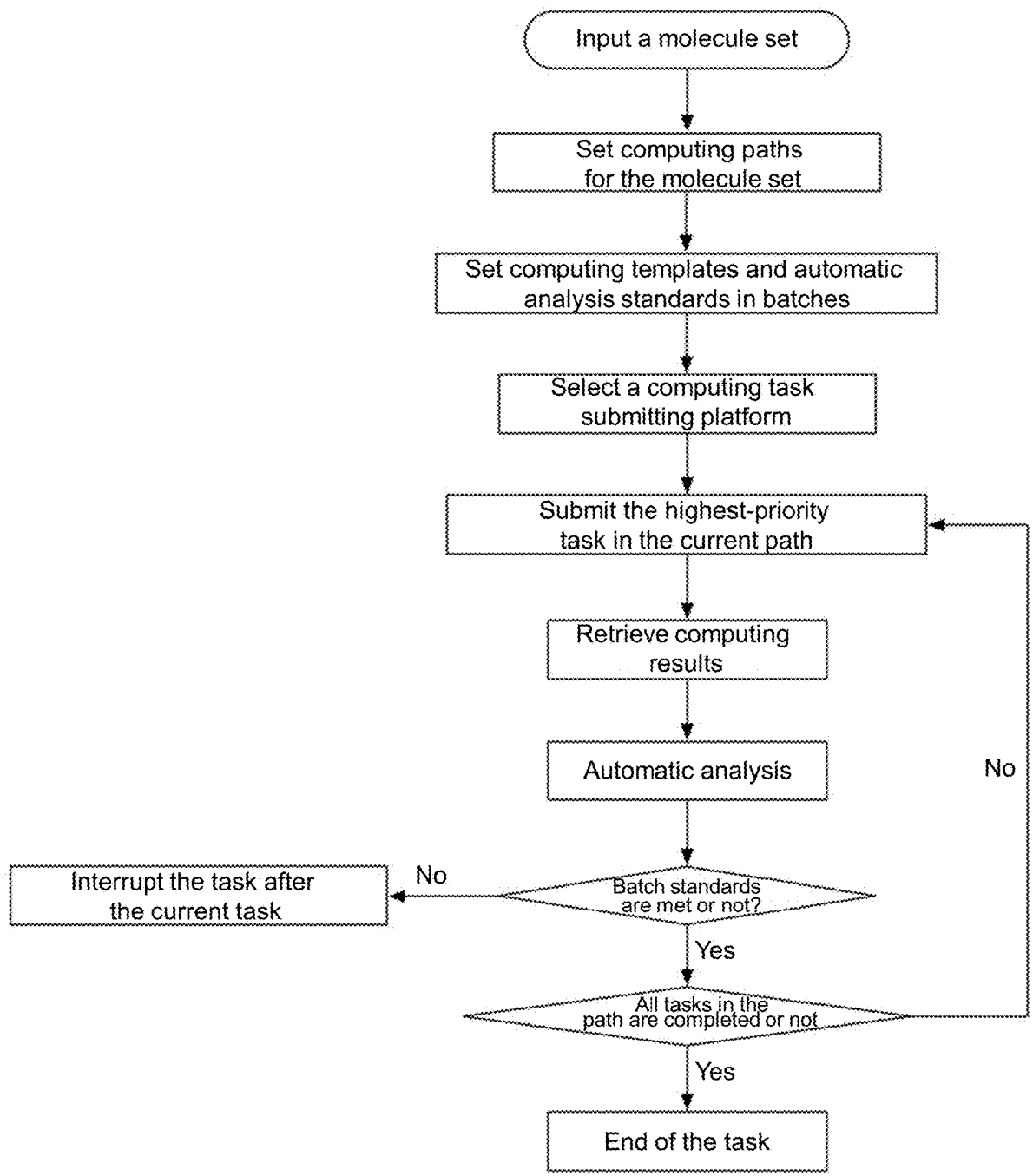
FIG. 4 is a flowchart under an automatic analysis scenario according to the present invention.

The specific application process applied to manual analysis is shown in FIG. 3;

The specific application process applied to automatic analysis is shown in FIG. 4;

The functional modules and processes in the figures are described below.

The building process of a molecular force field that is completed in one operation usually requires multiple computing steps. The application process of the manual analysis takes a typical molecular force field building computing task from its submission to analysis as an example.

In general, a batch of similar molecules will be selected as the input of the force field building fitting process. After the input, the following steps may be completed:

(1) Selecting Molecular Force Field Building Computing Templates

For different types of molecules, different parameters will need to be adjusted in the case of submission of a molecular force field building computing task. The system can automatically recommend computing parameters based on an input molecular type through a machine learning algorithm. Furthermore, the user may also adjust the parameters as needed so as to meet the requirement.

(2) Selecting a Computing Task Submitting Platform and Submitting the Computing Task The system supports submitting the computing task to local computing servers or clusters, supercomputing centers, and cloud services. Force field building workers usually implement computing by using local computing servers or supercomputing centers, and with the development of cloud services, cloud services can obviously provide a greater computing power to increase the building speed. However, general scientific research institutions do not have the ability to develop open interfaces of cloud services, and this obstacle can be overcome through the system.

(3) Retrieving Computing Results

After the computing task is completed, the system supports retrieving the computing result data to the local; and in consideration of security, the system also supports clearing computing data at the server or cloud and backing up important process data to the local.

Figure 5:
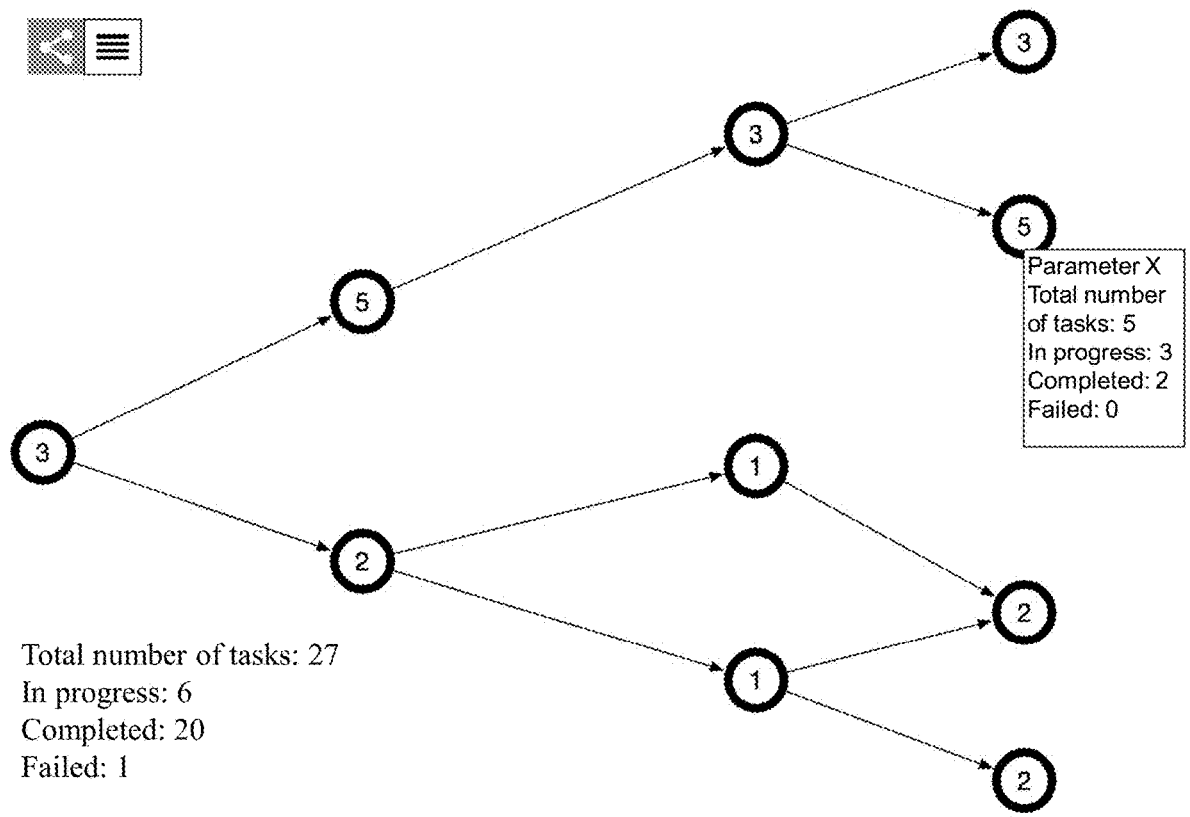
FIG. 5 is a view of computing task management applied to a force field data structure according to the present invention.

After the computing task is retrieved, it will be displayed according to the graph data structure of the force field parameters and with the force field parameters as indexes, as shown in FIG. 5.

(4) Analyzing the Results (a) Interactive Analysis

Figure 6:
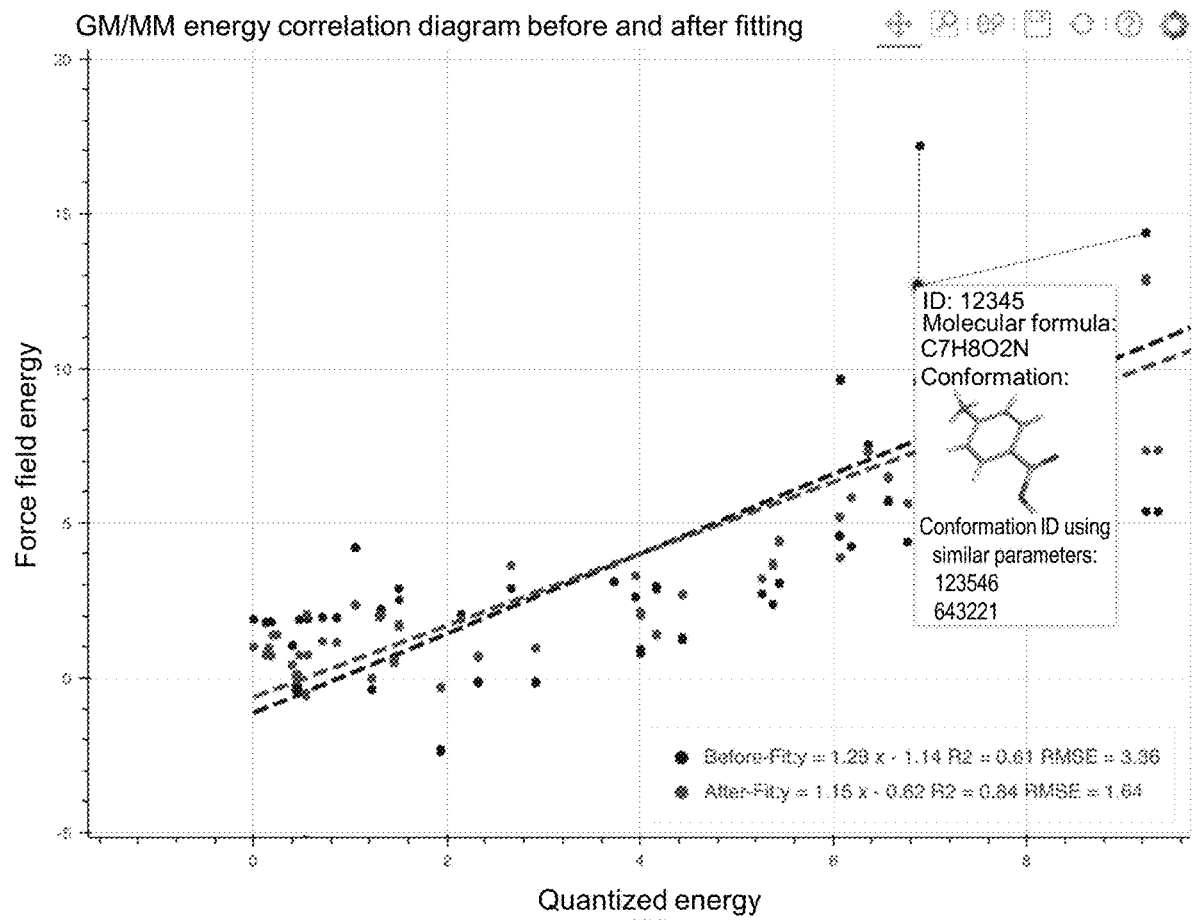
FIG. 6 is an interactive analysis view of computing results according to the present invention.

According to different computing templates, the system uses interactive analysis components corresponding to the computing templates to build an analysis report of the computing results. Taking the conventional molecular force field building result analysis mode as an example, it will include the comparisons in terms of energy, force, and structural parameters (bond length, bond angle, dihedral angle, anomalous dihedral angle, etc.) computed by the molecular mechanical method and the quantum mechanical method. Using the interactive analysis function, all the data of outliers can be quickly read and the analysis chart of data exceptions can be quickly located; the effect of a scatter plot is resented as an example, as shown in FIG. 6; in addition, computing functions may also be used to screen outliers in batches.

(b) Custom Analysis

Usually, the analysis function that comes with interactive analysis is enough to meet the general analysis needs, but there are situations where users will need to analyze other data. In this case, it is also possible to use the custom analysis feature to import the data required for analysis. Since the molecular data provided by the computing task is also based on the conformation number as the key index, it is possible to obtain the attributes or computing results of each conformation according to the conformation. Custom analysis supports a variety of chart types. In addition to common scatter plots, broken line charts, bar charts, and pie charts, it also supports box plots and violin plots that are sensitive to deviations and distributions, helping users to discover data issues more clearly.

In the case of the automatic analysis function, as shown in FIG. 4, it can be continuously and automatically executed by setting the computing path and the analysis standard. The specific steps and related functional modules are described below:

A. Setting Computing Paths of a Molecule Set

This system supports multi-task parallel submission, and needs to preset the molecular computing paths.

Figure 7:
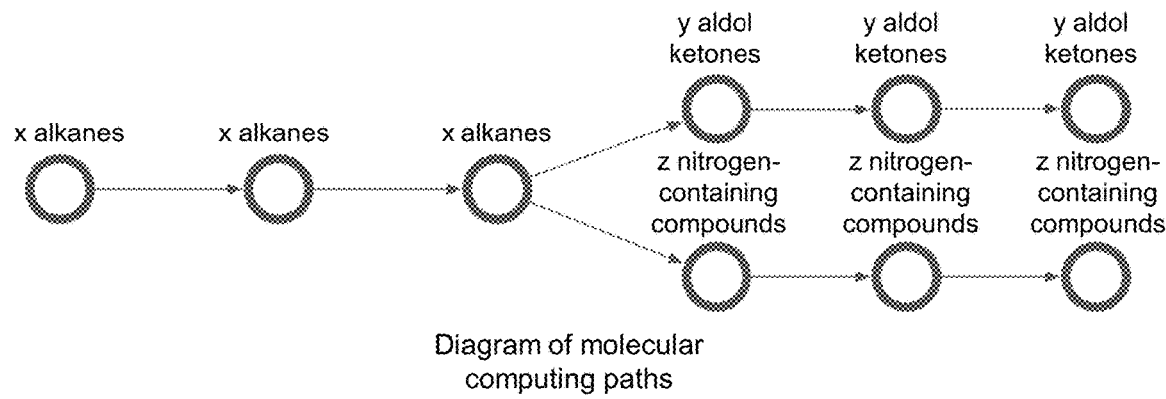
FIG. 7 is a schematic diagram of molecular computing path setting according to the present invention.

For example, a batch of molecules may have x alkanes, y aldol ketones, and z nitrogen-containing compounds. First, the x alkanes need to be subjected to fitting three times, and then the y aldol ketones and z nitrogen-containing compounds are simultaneously subjected to fitting three times. The paths in this case are shown in FIG. 7.

The molecules to be computed, the templates for the computing tasks, and the standards for automatic analysis need to be set on each path. The standards for automatic analysis are used to determine whether the fitting process of the current task meets the requirements, and if the requirements are met, the process proceeds to the next computing step; if the requirements are not met, the process is interrupted and the user is notified to reset the computing conditions.

B. Selecting a Computing Task Submitting Platform and Submitting the Computing Task Same as interactive analysis.

C. Retrieving Computing Results

Same as interactive analysis.

D. Automatic Analysis

After retrieving the computing results, since the standard for automatic analysis is preset, the system can automatically analyze the computing results of the task and save the analysis result after the calculation result is recovered. If the requirements are met, the computing will be continued until it is completed.

A complete molecular force field building process will be described as an example to illustrate the benefits.

Researchers at an institution plan to use 10,000 molecules to build a new molecular force field. The plan involves 100 tasks, and each time 100 molecules are fitted to build a force field.

By using this system, the person can plan the computing paths for 100 tasks in advance, and use the system's automatic matching template function to quickly set computing templates, and then submit the computing templates to the cloud for computing. If the traditional method is used, it is required to perform the submission for 100 times. Due to the use of automatic analysis, next task can be continued directly after the current task is completed, making full use of the spare time; in addition, the computing power on the cloud is more powerful and the computing speed is higher, so the molecular force field building efficiency is greatly improved.

When the computing is completed, the molecular force field building path, data structure, and the distribution and total amount of the computing tasks may be checked in the computing task management interface, and the global information of the current molecular force field building can be understood in a panoramic manner.

For the interactive analysis of the computing results, as shown in FIG. 6, the relevant information and conformation at any point can be checked, and it also help users compute other conformations using similar parameters to observe whether there are any exceptions; some computing functions may also be used to compute certain values, so as to quickly screen out a batch of abnormal molecules, which greatly improves the user's efficiency.

In addition, if necessary, custom analysis function may also be used to meet the individual needs of users.

What is claimed is:

1. A computing task management and analysis system for molecular force field parameter building, comprising:
    a memory;
    a processor, coupled to the memory, comprising a computing result analysis module and a computing task management module, wherein the computing result analysis module is connected with the computing task management module, and the computing task management module is connected with a force field building computing server through a cloud computing interface;
    wherein the computing result analysis module comprises interactive analysis, custom analysis, and automatic analysis;
    wherein the computing task management module comprises computing task submission graph data structure view, computing task template setting, computing path setting, and computing task result retrieving;
    wherein the task result retrieving is connected to the computing result analysis module, and the computing task submission is connected to the cloud computing interface.

2. An operation method of the computing task management and analysis system for molecular force field parameter building according to claim 1 comprising the following steps:
    (1) selecting molecular force field building computing templates,
    wherein the different parameters need to be adjusted in the case of submission of molecular force field building computing tasks for different types of molecules, the computing task management and analysis system automatically recommends computing parameters based on the types of input molecules through a machine learning algorithm, and the user also can adjust the parameters as needed; if automatic computing task submission is performed, molecular computing paths also can be set;
    (2) selecting a computing task submitting platform and submitting the computing tasks,
    wherein the computing task management and analysis system submits the computing tasks to local computing servers or clusters, supercomputing centers, and cloud services;
    (3) retrieving computing results,
    wherein after the computing tasks are completed, the computing task management and analysis system supports retrieving the computing result data to the local, clearing computing data at the servers or cloud, and backing up important process data to the local;
    wherein after the computing task results are retrieved, the computing task results are displayed according to the graph data structure of the force field parameters and with the force field parameters as indexes; and
    (4) analyzing the computing task results, wherein after the computing results are retrieved, the computing task management and analysis system will analyze the computing results;

wherein if an interactive analysis function is applied, data exceptions of the results can be quickly located and analyzed by using an analysis template;

wherein if a custom analysis function is applied, charts can be generated for analysis by analyzing the types of graphs and data displayed in a custom way;

wherein if an automatic analysis function is applied, whether the tasks meet the standards is determined in cooperation with the automatic computing task submission.

* * * * *